United States Patent [19]

Frazier

[11] 4,007,495
[45] Feb. 15, 1977

[54] PATELLO-FEMORAL PROTHESIS

[76] Inventor: Calvin H. Frazier, 1808 Verdugo Blvd., Glendale, Calif. 91208

[22] Filed: May 28, 1976

[21] Appl. No.: 690,986

[52] U.S. Cl. .................................. 3/1.91; 128/92 C
[51] Int. Cl.² .................................. A61F 1/24
[58] Field of Search .................. 3/1, 1.9–1.911; 128/92 C

[56] References Cited

UNITED STATES PATENTS

| | | | |
|---|---|---|---|
| 3,506,982 | 4/1970 | Steffee | 3/1.91 |
| 3,760,427 | 9/1973 | Schultz | 3/1.91 |
| 3,806,961 | 4/1974 | Muller | 3/1.913 |
| 3,878,566 | 4/1975 | Bechtol | 3/1.91 |

*Primary Examiner*—Ronald L. Frinks
*Attorney, Agent, or Firm*—Robert C. Comstock

[57] ABSTRACT

A patello-femoral prosthesis comprising a patellar prosthesis and a femoral prosthesis which are connected to each other for relative sliding movement. The connecting means comprises a keyhole shaped slot formed in one prosthesis, and a complementarily formed collar button shaped projection carried by the other prosthesis. The projection has an enlargement on its outer end which is mounted in the slot for sliding movement along the slot. The engagement between the projection and slot prevents undesirable separation or dislocation of the prostheses with respect to each other. In one embodiment, the slot is adapted to be expanded by engagement with the projection to permit the projection to move into the slot.

7 Claims, 4 Drawing Figures

PATELLO-FEMORAL PROTHESIS

BACKGROUND OF THE INVENTION

1. Field of the Invention:

The invention relates to a prosthesis device for the patello-femoral joint.

2. Description of the Prior Art:

Patello-femoral prostheses are known which are used to replace the articulating surfaces of the patello-femoral joint.

U.S. Pat. No. 3,878,566 discloses such a device comprising a femoral prosthesis which is attached to the femur and a patellar prosthesis which is secured to the patella. The patellar prosthesis has a ridge which slidably moves within a trough-like indentation in the femoral prosthesis.

Other patents disclose various other types of prostheses which are similar in their structure and operation.

In all of the prior art devices there is nothing to prevent the component prostheses from coming apart from each other in use. If the ridge moves out of the indentation, the prostheses may be displaced laterally or medially with respect to each other, which is extremely undesirable.

SUMMARY OF THE INVENTION

The primary object of the present invention is to provide a patello-femoral prosthesis of the type described in which there is a slidable but substantially inseparable engagement between two component prostheses which prevents them from becoming separated and which renders impossible any undesirable lateral or medial displacement of the prostheses with respect to each other.

In essence, my invention contemplates a projection carried by one prosthesis which extends into a keyhole shaped slot formed on the other prosthesis. The projection has a collar button type of configuration which includes an enlargement of its end which fits within an enlarged inner portion of the slot.

The connection between the prostheses may be made in one of two ways. One of the members, preferably the slot, may be formed in somewhat compressible material such as plastic which may be slightly expanded in order to permit the projection to pass into the slot. The slot then resumes its normal dimensions and configuration and the projection is held against movement out of the slot. The enlargement will not move out of the slot because the operation of the prosthesis in use will not apply the type and/or amount of pressure which would be required to pull the enlargement out through the narrow portion of the slot.

The other type of connection which may be used is to form the projection of rigid uncompressible material and to slide it into the slot through an opening formed at one end, preferably the top of the slot. The slot is preferably slightly elongated for this purpose so that in the use of the prosthesis the projection cannot be extended in such a manner as to move it back out through the entrance of the slot.

There is accordingly a sliding engagement between the two prosthesis component members of the same type which is found in the prior art, with the added improvement of a secure interlocking engagement between the sliding members which makes separation unlikely and helps to prevent undesirable sideward slipping movement of the components in use.

It is accordingly among the objects of the invention to provide a patellar-femoral prosthesis having all of the advantages and benefits set forth above and described in further detail hereinafter in this specification.

The invention also comprises such other objections, advantages and capabilities as will later more fully appear and which are inherently possessed by the invention.

While there are shown in the accompanying drawings preferred embodiments of the invention, it should be understood that the same are susceptible of modification and change without departing from the spirit of the invention.

DESCRIPTION OF THE PREFERRED EMBODIMENTS

Figure 1:
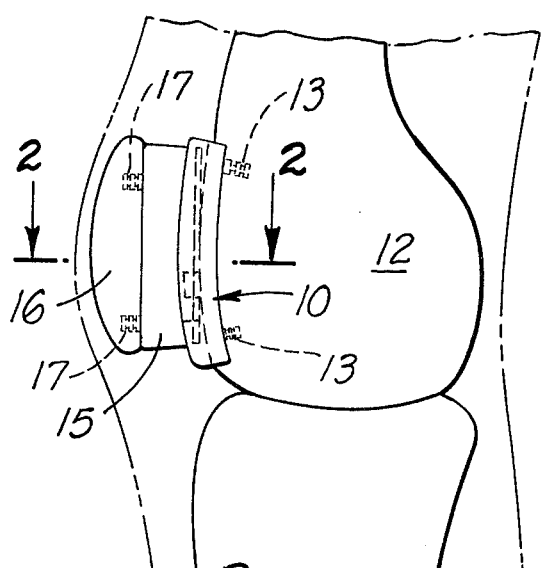
FIG. 1 is a side elevational view of a first embodiment of the patellar prosthesis in use on a knee joint.
Figure 2:
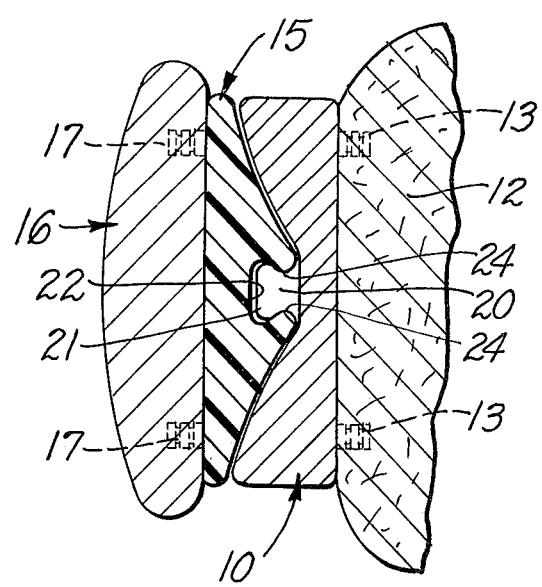
FIG. 2 is a sectional view of the same taken on line 2—2 of FIG. 1.

A first preferred embodiment which has been selected to illustrate my invention includes a first component comprising a femoral prosthesis 10, which is adapted to be attached to the patellar facet of the femur 12. The femoral prosthesis 10 is preferably secured by means of conventional bone cement. A plurality of fastening members in the form of studs 13 or the like may be inserted into openings drilled into the femur 12 and held therein by the cement.

The second component comprises a patellar prosthesis 15, which is adapted to be attached to the inner surface of the patellar 16 by the same means comprising bone cement and studs 17 extending into openings drilled into the patella 16.

The structures set forth above and the means for emplacing them on the body are well known to those skilled in the art and are fully described in the foregoing patents and in medical and trade literature.

The novel feature of the present invention resides in the connective relationship between the femoral prosthesis 10 and the patellar prosthesis 15.

The femoral prosthesis 10 is preferably formed of steel or other substantially rigid material. It is provided at its midportion along substantially its entire length with a projection 20 having an enlargement 21 formed on the end of a neck which extends between the enlargement 21 and the femoral prosthesis 10. The projection 20 is accordingly shaped like a collar button in cross section.

The midportion of the patellar prosthesis 15 is provided along substantially its entire length with a slot 22 which is formed complementarily to the projection 20 of the femoral prosthesis 10. The slot 22 has a narrow entrance disposed between a pair of spaced walls 24 which are preferably formed integrally with the patellar prosthesis 15. Inwardly from the entrance, the slot 22 has an enlarged inner portion which is adapted to slidably receive the enlargement 21 formed on the end of the projection 20. The slot 22 is shaped like a keyhole in cross section.

The patellar prosthesis 15, or at least the portion forming the walls 24 of the slot 22, is preferably formed of high density polyethylene or similar plastic material having a limited degree of deformability.

In use, the femoral prosthesis 10 is mounted on the femur 12 and the patellar prosthesis 15 is mounted on the patella 16 in the manner described above. The two components of the complete prosthesis are then connected together by pressing the patella 16 and the patellar prosthesis 15 toward the femoral prosthesis 10 with sufficient pressure to deform the walls 24 of the slot 22 to a slightly larger width, so that the enlargement 21 can pass between the walls 24 through the entrance of the slot and into the enlarged inner portion of the slot 22.

The action involved is similar to that of a snap bead, with the walls 24 being expanded sufficiently to pass the enlargement 21 through the entrance and then returning back to normal configuration to prevent its withdrawal from the slot 22.

In the use of the complete prosthesis, the engagement between the projection 20 and the slot 22 acts to prevent any undesirable lateral or medial slipping movement or displacement of the patella 16 with respect to the femur 12. Separation the patellar prosthesis 15 from the femoral prosthesis 10 is unlikely because in the use of the device no strain or force is exerted against the prosthesis components of a type and amount which could cause the enlargement 21 to move back out through the entrance of the slot 22.

Figure 3:
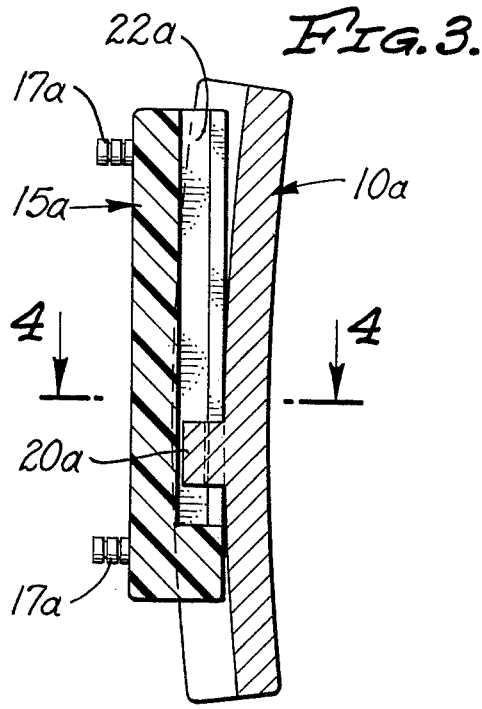
FIG. 3 is a longitudinal sectional view of a second preferred embodiment of the patellar-femoral prosthesis with the two parts assembled, but the knee joint omitted.
Figure 4:
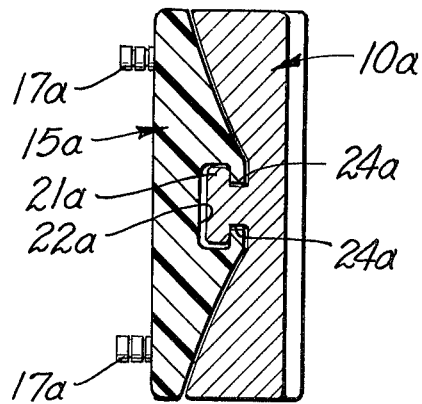
FIG. 4 is a sectional view of the same taken on line 4—4 of FIG. 3.

A second preferred embodiment of the invention is shown in FIGS. 3 and 4 of the drawings. For convenience, the same reference numerals are applied to the same elements of the second embodiment with the addition of the letter a. The only difference between this embodiment of the invention and the first embodiment described above is that the patellar prosthesis 15, or at least the walls 24 of the slot 22 cannot be widened or deformed. The enlargement 21a is also somewhat wider in configuration so that it cannot possibly be moved through the entrance of the slot 22a.

The second embodiment of the invention is assembled in a different manner from the first embodiment. Both of the prosthesis components are preferably made slightly longer than normal at their upper ends. The projection 20a is slidably moved into the upper end of the slot 22a. The prosthesis components are dimensioned so that in use the patellar prosthesis 15a cannot possibly be moved upwardly to an extent sufficient to move it out through the top of the slot 22a of the femoral prosthesis 10a.

It will be understood by those skilled in the art that the arrangement of the connecting parts may be reversed from that shown and described herein, with the projection and enlargement being formed on or carried by the patellar prosthesis and the slot being formed on the femoral prosthesis.

I claim:

1. A patello-femoral prosthesis comprising a patellar prosthesis which is dimensioned and contoured complementarily to the natural patella and having one side thereof which is adapted to fit against and be secured to the inner surface of the natural patella, and a femoral prosthesis which is dimensioned and contoured complementarily to the portion of the outer surface of the natural femur which the natural patella normally overlies, said femoral prosthesis having one side thereof which is adapted to fit against and be secured to the outer surface of the natural femur, the opposite side of said femoral prosthesis having a substantially concave configuration, the opposite side of said patellar prosthesis having a substantially convex portion, said convex and concave portions having formed complementarily to and adapted to engage each other, connector means for connecting said prosthesis for sliding movement with respect to each other, said connector means comprising a substantially keyhole shaped slot formed in one of said prostheses, said slot having a pair of spaced walls forming a narrow entrance portion and an enlarged inner portion, and a complementarily formed collar button shaped projection carried by the other of said prostheses, said projection having an enlargement on the outer end thereof and a narrow portion disposed inwardly from said enlargement, said projection adapted to be mounted in said slot for sliding movement along said slot, with the engagement between said enlargement and slot preventing undesirable separation or dislocation of said prostheses with respect to each other during the use of said patello-femoral prosthesis.

2. The structure described in claim 1, said slot being formed in plastic material having a limited degree of deformability, the walls of said slot adapted to be expanded by engagement with said projection as said projection is pressed through said narrow entrance portion into the enlarged inner portion of said slot, the walls of said slot upon the release of pressure thereon returning by their own reilience back to their normal configuration.

3. The structure described in claim 1, said enlargement being slightly wider than the entrance to said slot so that said enlargement cannot pass through said entrance, said slot having an opening at the upper end thereof through which said projection may be inserted into said slot, said slot being of sufficient length so that said projection cannot be moved out through the upper end of said slot when said prosthesis is in use.

4. The structure described in claim 1, said projection being carried by said femoral prosthesis and said slot being formed in said patellar prosthesis.

5. The structure described in claim 2, said projection being carried by said femoral prosthesis and said slot being formed in said patellar prosthesis.

6. The structure described in claim 5, said walls of said slot being formed of polyethylene.

7. The structure described in claim 3, said femoral prosthesis being formed of steel and said projection being formed integrally with said femoral prosthesis.

* * * * *